United States Patent
Micetich et al.

(10) Patent No.: US 6,916,803 B2
(45) Date of Patent: Jul. 12, 2005

(54) 3-(HETEROARYL ACETAMIDO)-2-OXO-AZETIDINE-1-SULFONIC ACIDS DERIVATIVES AS ANTIBACTERIAL AGENTS

(75) Inventors: Ronald George Micetich, Alberta (CA); Samarendra Maiti, Alberta (CA); Charles Fiakpui, Alberta (CA); George Thomas, Alberta (CA); Andhe V. Narender Reddy, Alberta (CA); Sameeh M. Salama, Alberta (CA); Rajeshwar Singh, Alberta (CA)

(73) Assignee: Pantherix, Ltd. (GB)

( * ) Notice: Subject to any disclaimer, the term of this patent is extended or adjusted under 35 U.S.C. 154(b) by 78 days.

(21) Appl. No.: 10/363,222

(22) PCT Filed: Sep. 14, 2001

(86) PCT No.: PCT/IB01/02115

§ 371 (c)(1),
(2), (4) Date: Feb. 27, 2003

(87) PCT Pub. No.: WO02/22613

PCT Pub. Date: Mar. 21, 2002

(65) Prior Publication Data

US 2004/0019203 A1 Jan. 29, 2004

Related U.S. Application Data

(60) Provisional application No. 60/232,617, filed on Sep. 14, 2000.

(51) Int. Cl.[7] ............... C07D 227/087; A61K 31/4439; A61P 31/04
(52) U.S. Cl. .................... 514/210.15; 540/355
(58) Field of Search ............... 514/540, 355, 514/210.15

(56) References Cited

U.S. PATENT DOCUMENTS 5,112,968 A   5/1992  Treuner 5,250,691 A * 10/1993 Straub et al. ............... 544/355

FOREIGN PATENT DOCUMENTS

| EP | 0 204 207 A | 12/1986 |
|----|-------------|---------|
| GB | 2 218 095 A | 11/1989 |
| WO | WO 98 47895 A | 10/1998 |
| WO | WO 99 10324 A | 3/1999 |

OTHER PUBLICATIONS

Nishida, K. et al. (1999) "In vitro and in vivo activities of Syn2190, a novel beta–lactamase Inhibitor" *Antimicrobial Agents and Chemotherapy* 43(8):1895–1900.

* cited by examiner

*Primary Examiner*—Mark L. Berch
(74) *Attorney, Agent, or Firm*—Saliwanchik, Lloyd & Saliwanchik

(57) ABSTRACT

The present invention relates to novel Syn isomers of racemates and optical isomers of 3-(heteroaryl acetamido)-2-oxo-azetidine-1-sulfonic acids of the following formula:

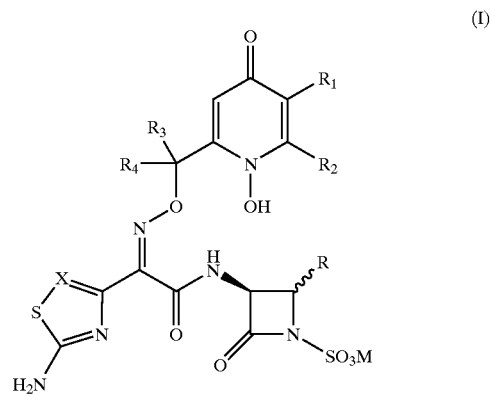

and their use in treating infections caused by gram-negative pathogenic bacteria.

19 Claims, No Drawings

3-(HETEROARYL ACETAMIDO)-2-OXO-AZETIDINE-1-SULFONIC ACIDS DERIVATIVES AS ANTIBACTERIAL AGENTS

This application is a National Stage Application of International Application Number PCT/IB01/02115, published, pursuant to PCT Article 21(2) which claims benefit of 60/232617, Sep. 14, 2000.

The present invention relates to novel Syn isomers of racemates and optical isomers of 3-(heteroaryl acetamido)-2-oxo-azetidine-1-sulfonic acids and its use in treating the infections caused by gram-negative pathogenic bacteria.

BACKGROUND OF INVENTION

Bacteria are very adaptable microorganisms that possess the ability to adapt and to survive under adverse conditions. Doctors in hospitals and clinics around the world are losing the battle against an onslaught of new drug resistant bacterial infections including those caused by Staphylococci, Streptococci, Enterococci and Pseudomonas.

Bacterial resistance to the current antibiotics has been on a steep rise due to the alteration of the target, a change in the permeability pattern or by efflux of active ingredient and by deactivation of the antibiotic before reaching the active site.

The β-lactam antibiotics (penicillins, cephalosporins, monobactams and carbapenems) are the most widely used group of antibiotics for the treatment of many infectious diseases, because of proven clinical efficacy and their excellent safety profile. Bacterial resistance towards gram-positive pathogens against β-lactam antibiotics is mainly due to the alteration of penicillin binding proteins (PBP's), efflux of active ingredient and deactivation of active ingredient. Whereas bacterial resistance towards gram-negative pathogens against β-lactam antibiotics in addition to those of the gram-positive pathogen, also are due to changes in outer membrane permeability pattern.

To overcome the changes in outer membrane permeability, in recent years a number of β-lactam compounds (cephem and monobactam) containing an iron chelating catecholic and dihydroxypyridone groups have been reported (29$^{Th}$ ICAAC, Houston Tex., Sep. 18, 1989, abstract no. 355, 356; 30$^{th}$ ICAAC, Atlanta, Ga., Oct. 22, 1990, abstract no. 458; Antimicrobial Agents and chemotherapy 1991, 35, 104–110). The potent activity of these compounds is due to their utilization of the TonB-dependent iron transport systems for transport across the bacterial outer membrane (Antimicrobial Agents and chemotherapy 1995, 39, 613–619).

Monobactams are a class of antibacterial agents and have been used to treat infections caused by gram-negative microorganisms. Currently Aztreonam and Carumonam are in clinical use. Quinoxaline directly attached to an oxime side chain of the monobactam nucleus is under development (Curr. Opin. Anti-infect. Drugs 1999, 1(1), 96–100; Antimicrobial Agents and Chemotherapy 1997, 41, 1010–1016). Further dihydroxypyridine through a methylene spacer attached to an oxime side chain in the anti orientation is reported as β-lactamase inhibitor (U.S. Pat. No. 5,888,998 (1999)).

The present invention describes a class of compound in which a dihydroxypyridone group is directly or through a suitable spacer attached to an oxime side chain in a monobactam nucleus and its use to treat gram-negative infections, particularly those caused by Pseudomonas. Pseudomonas aeruginosa continues to be a very frequent opportunistic pathogen, capable of causing a wide variety of infections in the immunocompromised patient. These infections are often associated with significant morbidity and are difficult to treat.

SUMMARY OF THE INVENTION

It is an objective of the present invention to provide novel Syn isomers of racemates and optical isomers of 3-(heteroaryl acetamido)-2-oxo-azetidine-1-sulfonic acids of formula I having antibacterial activity against gram-negative pathogenic bacteria, particularly *Pseudomonas* strains.

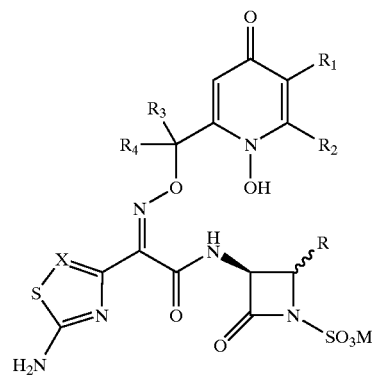

(I)

It is a further object of the invention to provide pharmaceutical compositions comprising the compound of formula I with a pharmaceutically acceptable carrier or diluent.

It is an additional object of the invention to provide a method for treatment of bacterial infections caused by gram-negative pathogenic bacteria including *Pseudomonas*.

DETAILED DESCRIPTION OF THE INVENTION

In accordance with the present invention, there is provided novel Syn isomers of recemates and optical isomers of 3-(heteroaryl acetamido)-2-oxo-azetidine-1-sulfonic acids of formula I

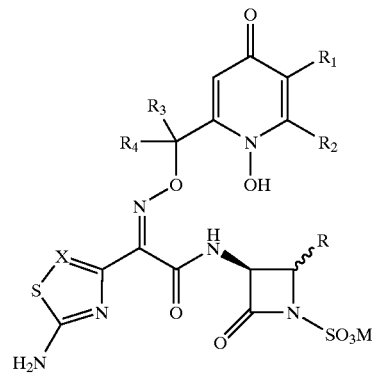

(I)

Wherein

M is a hydrogen or a pharmaceutically acceptable salt forming cation;

X is CH, N or C-halo;

R is $C_1$–$C_3$ allyl which is unsubstituted or substituted with at least one of (a) a halogen atom (b) $OR_5$ wherein $R_5$ is hydrogen, $CONH_2$ or 2,5-dihydroxy-4-oxo-1,4-dihydropyridin-2-yl-carbonyl and wherein a $C_1$ alkyl may not be substituted with both a halogen atom and $OR_5$.

$R_1$ and $R_2$ independently are OH, COOH, $CONH_2$, optionally substituted phenyl or $C_1$–$C_3$ alkyl; or $R_1$ and $R_2$ together are —O—CH=CH—$CH_2$—, —O—$CH_2$—$CH_2$—O—, —$CH_2$—$CH_2$—$CH_2$—, —$CH_2$—$CH_2$—$CH_2$—$CH_2$—, —CH=CH—CH=CH— or —CH=C(OH)—C(OH)=CH— which together with the carbon atoms to which they are bound form a 5 membered or six membered cyclic ring $R_3$ and $R_4$ independently are hydrogen, optionally substituted $C_1$–$C_3$ alkyl, optionally substituted phenyl or $C_3$–$C_6$ cycloalkyl;

$R_3$ and $R_4$ together are $C_3$–$C_6$ cycloalkyl.

As used herein, the term "$C_1$–$C_3$ alkyl" means a straight or branch chain alkyl having 1–3 carbon atom selected from methyl, ethyl, propyl and isopropyl.

As used herein, the term "$C_3$–$C_6$ cycloalkyl" means a saturated alicyclic moiety having 3–6 carbon atoms selected from cyclopropyl, cyclobutyl, cyclopentyl and cyclohexyl.

As used herein, the term "halogen atom" means fluorine, chlorine, or bromine.

As used herein, the term "substituted" as applied to a group means substituted with 1, 2 or 3 substituents selected from OH, $NH_2$, dimethylamino, a halogen atom, $OCH_3$, COOH, $CONH_2$, $NO_2$ or CN.

As used herein, the term "racemate" means the mixture of diastereoisomers having zero optical rotation of the molecule of formula I.

As used herein, the term "optical isomers" means pure single R and S diastereoisomers at the asymmetric carbon atoms present in the molecule of formula I.

As used herein the term "pharmaceutically acceptable salt forming cation" means alkali metals (e.g. Sodium, Potassium), alkaline earth metals (e.g. Calcium, Magnesium), organic bases (e.g. triethylamine, ethanolamine, n-methylmorpholine) or basic amino acids (e.g. lysine, arginine, orithine or histidine). Moreover when M is hydrogen in formula I, it can form zwitterions (inner salt or internal salt) by interacting with a basic nitrogen atom present in the molecule of formula I.

In accordance with the preferred embodiment of the present invention, there is provided novel Syn isomers of racemates and optical isomers of 3-(heteroaryl acetamido)-2-oxo-azetidine-1-sulfonic acids and of formula I

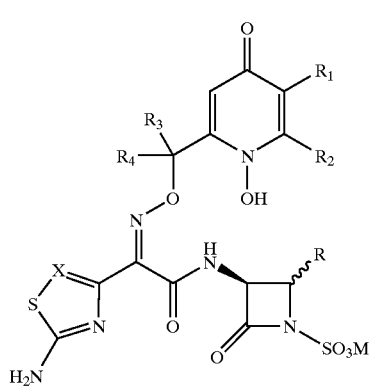

(I)

Wherein

M is a hydrogen or pharmaceutically acceptable salt forming cation;

X is CH;

R is $CH_3$, $CH_2F$ or $CH_2OCONH_2$.

$R_1$ is OH $R_2$ is Hydrogen;

$R_1$ and $R_2$ together is —CH=C(OH)—C(OH)=CH— which forms six member cyclic ring $R_3$ and $R_4$ independently is hydrogen;

$R_3$ and $R_4$ together is cyclopropyl;

As used herein, the term "racemate" means the mixture of diastereoisomers having zero optical rotation of the molecule of formula I.

As used herein, the term "optical isomers" means pure single R and S diastereoisomers at the asymmetric carbon atoms present in the molecule of formula I.

As used herein the term "pharmaceutically acceptable salt forming cation" means alkali metals (e.g. Sodium, Potassium). Moreover when M is hydrogen in formula I, it can form zwitterion (inner salt or internal salt) by interacting with a basic nitrogen atom present in the molecule of formula I.

The compounds of this invention can be used to treat bacterial infections caused by gram-negative bacteria, including but not limited to *Pseudomonas E. eloaecae, C. freundii, M. Morganii, K. paeumoniae,* and *E. Coli* alone or in combination with other drugs in mammals including humans. The compounds may be administered in pharmaceutical dosage forms including parenteral preparation such as injections, suppositories, aerosols and the like, and oral preparations such as tablets, coated tablets, powders, granules, capsules, liquids and the like. The above preparations are formulated in manners well known to the art.

For the formulation of solid preparations for oral administration, an excipient, and if desired, a binder, disintegrator, lubricant, coloring agent, corrigent, flavor etc. are added to the compound of the invention, and then tablets, coated tablets, granules, powders, capsules or the like are prepared in a conventional manner.

For the formulation of injections, a pH adjusting agent, buffer, stabilizer, isotonic agent, local anesthetic or the like is added to the active ingredient of the invention, and injections for subcutaneous, intramuscular or intravenous administration can be prepared in the conventional manner.

For the formulation of suppositories, a base, and if desired, surfactants are added to the active ingredient of the invention, and the suppositories are prepared in a conventional manner.

The excipients useful for solid preparations for oral administration are those generally used in the art, and the useful examples are excipients such as lactose, sucrose, sodium chloride, starches, calcium carbonate, kaolin, crystalline cellulose, methyl cellulose, glycerin, sodium alginate, gum arabic and the like, binders such as polyvinyl alcohol, polyvinyl ether, polyvinyl pyrrolidone, ethyl cellulose, gum arabic, schellac, sucrose, water, ethanol propanol, carboxymethyl cellulose, potassium phosphate and the like, lubricants such as magnesium stearate, talc and the like, and further include additives such as usual known coloring agents, disintegrators and the like. Examples of bases useful for the formulation of suppositories are oleaginous bases such as cacao butter, polyethylene glycol, lanolin, fatty acid triglycerides, witepsol (trademark, Dynamite Nobel Co. Ltd.) and the like. Liquid preparations may be in the form of aqueous or oleaginous suspension, solution, syrup, elixir and the like, which can be prepared by a conventional way using additives.

The amount of the compound I of the invention incorporated into the pharmaceutical composition of the invention varies with the dosage form, solubility and chemical properties of the compound, administration route, administration scheme and the like. Preferably the amount is about 1 to 25 w/w % in the case of oral preparations, and about 0.1 to 5 w/w % in the case of injections which are parenteral preparations.

The dosage of the compound I of the invention is suitably determined depending on the individual cases taking symptoms, age and sex of the subject and the like into consideration. Usually the dosage in the case of oral administration is about 50 to 1500 mg per day for an adult in 2 to 4 divided doses, and the dosage in the case of injection, for example, by intravenous administration is 2 ml (about 1 to 100 mg) which is administered once a day for adults wherein the injection may be diluted with physiological saline or glucose injection liquid if so desired, and slowly administered over at least 5 minutes. The dosage in case of suppositories is about 1 to 1000 mg which is administered once or twice a day at an interval of 6 to 12 hours wherein the suppositories are administered by insertion into the rectum.

The compounds of the present invention having the formula I can be prepared by reacting 3-amino-azetidine-2-one sulfonic acid of formula (II) with heteroaryl carboxylic acid of formula III followed by deprotection of the protecting group.

Scheme 1

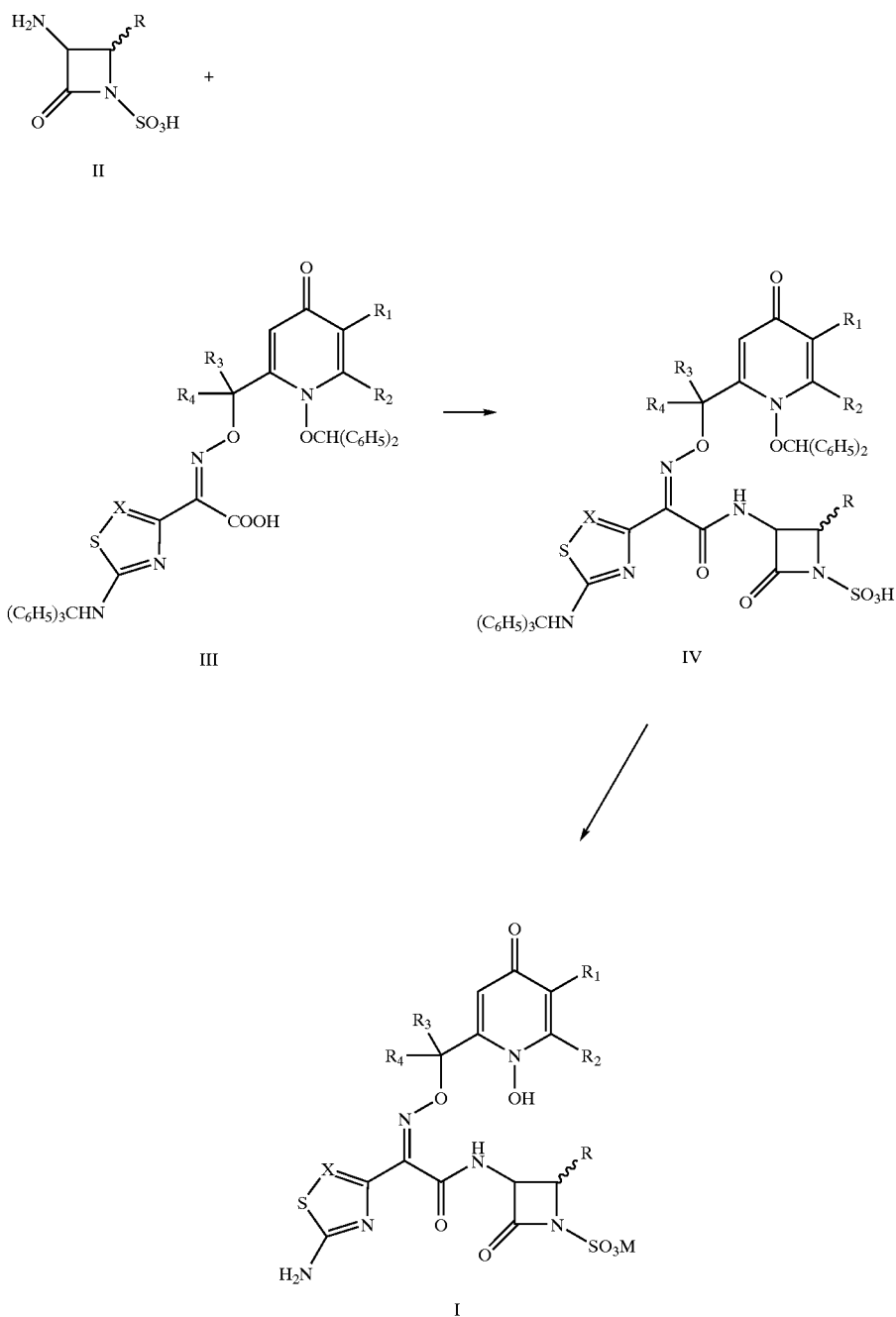

Certain derivatives of general formula IV were prepared by coupling of 3-amino-azetidine-2-one sulfonic acid (II) with a heteroaryl carboxylic acid (III) in presence of dicyclohexylcarbodiimide (DCC) or with an acid chloride of compound (III) in presence of base, or with an activated ester of compound (III) within the skill of the arts.

Alternatively, compounds of formula I can also be prepared as follows:

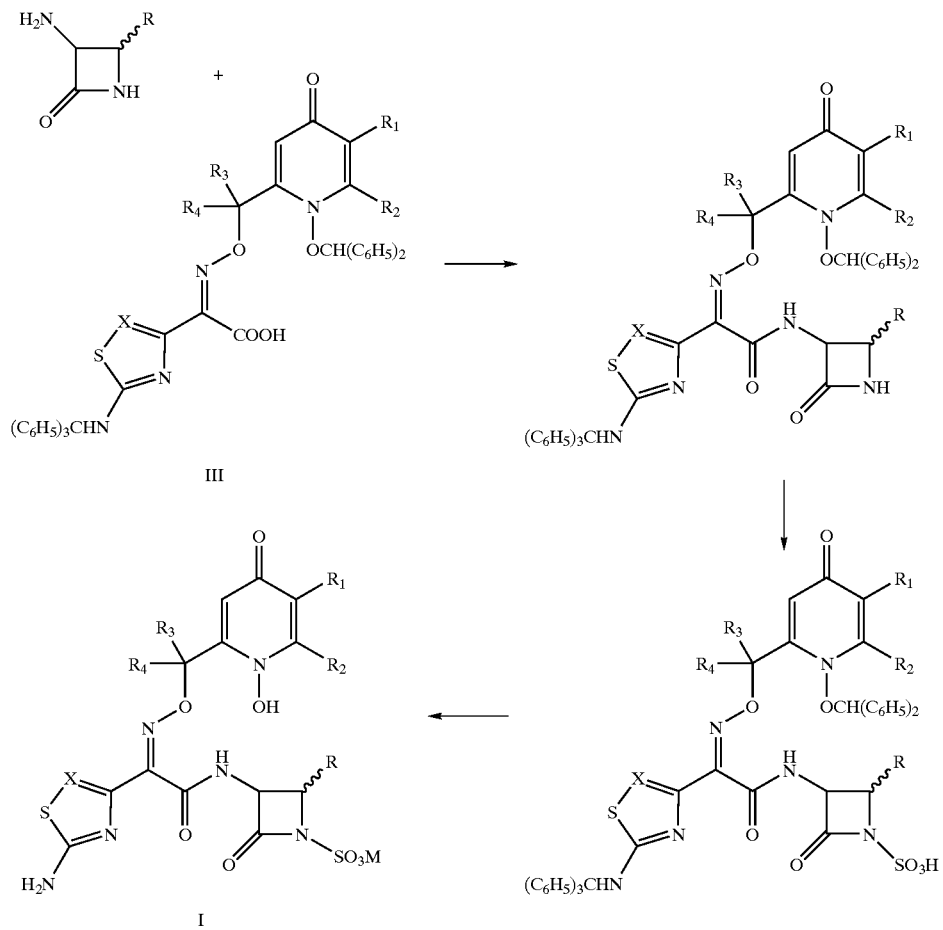

The preparation of compound II (R=$CH_3$) was carried out by following the synthetic scheme 2 as described in J. Org. Chem. 1982, 47, 5160–5167.

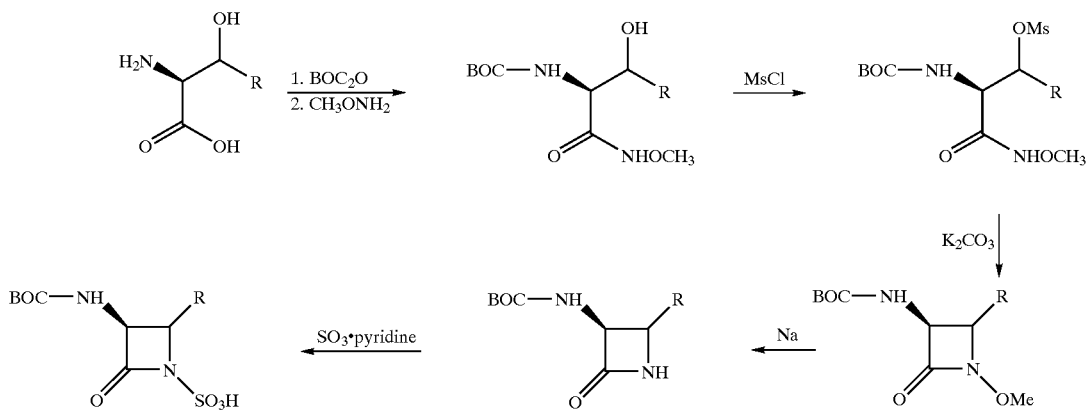

R = trans $CH_3$, Threonine derived
R = cis $CH_3$, allo-threonine derived

The preparation of compound II (R=CH$_2$F, CH$_2$OCONH$_2$) was carried out by following the synthetic scheme 3 from common intermediate compound V as described in J. Antibiotics 1983, 36, 1201–1204 and J. Antibiotics 1985, 38, 346–357.

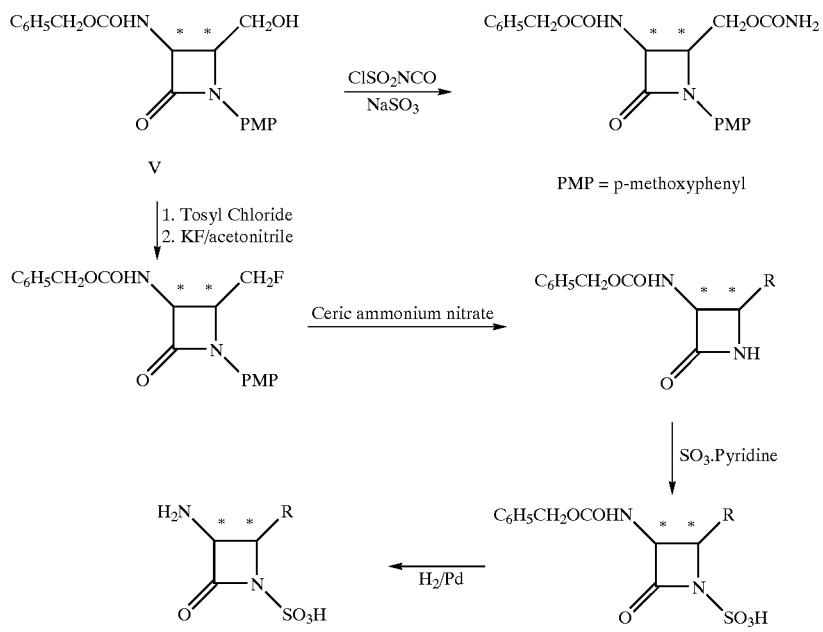

Scheme 3

PMP = p-methoxyphenyl

The common intermediate compound V was prepared by following the synthetic route as described in scheme 4. The distereoisimers of compound VI are separated by optical resolution methods (J. Antibiotics 1985, 38, 346).

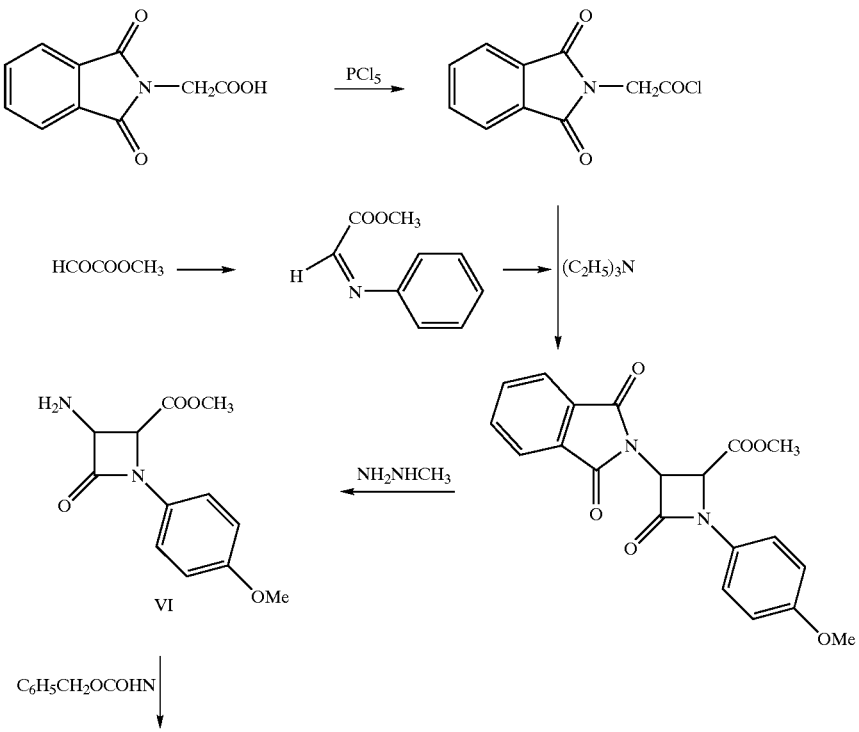

Scheme 4

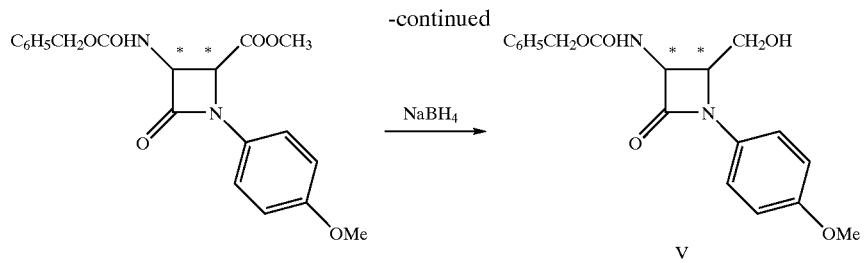

*represents cis isomers at carbon 3 and 4

The preparation of compounds III was done by reacting 2-heteroaryl-2-oxo acetic acid (VII) with O-heteroaryl hydroxyl amine (VIII) at room temperature and afforded exclusively the syn-isomer. The preparation of compound VIII was done as described in Scheme 5 starting from heteroarylmethanol (J. Antibiotics 1990, 43, 189–198).

Scheme 5

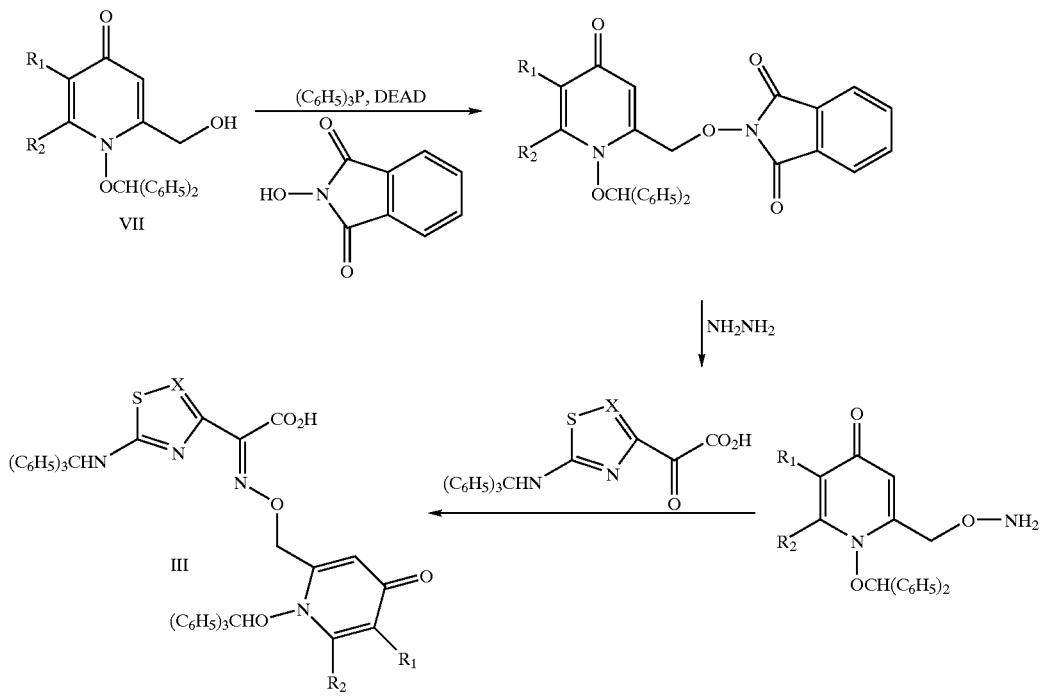

DEAD = Diethylazodicarboxylate

In the above descriptions (scheme 1–5), the reactants are reacted together with a suitable solvent at elevated or low temperatures for sufficient time to allow the reaction to proceed to completion. The reaction conditions will depend upon the nature and reactivity of the reactants. Wherever a base is used in a reaction, they are selected from triethylamine, tributylamine, trioctylamine, pyridine, 4-dimethylaminopyridine, diisopropylethylamine, 1,5-diazabicyclo[4,3,0]non-5-ene, 1,8-diazabicyclo[5,4,0]undec-7-ene, sodium carbonate, sodium bicarbonate, potassium carbonate, potassium bicarbonate or cesium carbonate.

The deprotection of the protective group is carried out either by hydrogenation or by hydrolysis with appropriate acids such as hydrochloric acid, trifluoroacetic acid or acetic acid in solvent such as methanol, ethanol, propanol or ethyl acetate. The hydrogenation reaction is usually carried out in the presence of a metal catalyst, such as Pd, Pt, or Rh, under normal pressure to high pressure.

The solvents of choice for the reaction are selected based upon the reactants used and from such solvents as benzene, toluene, acetonitrile, tetrahydrofuran, ethanol, methanol, chloroform, ethyl acetate, methylene chloride, dimethyl formamide, dimethyl sulfoxide, hexamethyl phosphoric triamide, or the like. Solvent mixtures may also be utilized.

Reaction temperatures would generally range from between −70° C. to 150° C. The preferred molar ratio of reactants is 1:1 to 1:5. The reaction time range from 0.5 to 72 hours, depending on the reactants.

The present invention is further illustrated by the following non-limiting examples.

EXAMPLE 1

(3S)-trans-3-[(2-Amino)thiazol-4-yl)-(Z)-2-{(1,5-dihydroxy-4-pyridon-2-yl methoxy)imino}acetamido]-4-methyl-2-oxoazetidine-1-sulfonic acid, sodium salt Step 1: 1,5-Dibenzhydryloxy-2-(N-phthalimido)oxymethyl-4-pyridone

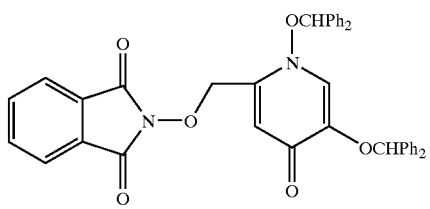

A solution of 1,5-dibenzhydryloxy-2-hydroxymethyl-4-pyridone (20.0 g, 0.041 mol) and N-hydroxyphthalimide (6.64 g, 0.048 mol) in a mixture of THF (200 ml) and dry DMF (200 ml) was treated with triphenyl phosphene under nitrogen and cooled to 0° C. The reaction mixture was then added with diethyl azodicarboxylate dropwise over 10 min., stirred at 0° C. for 1 h then diluted with ethyl acetate and water. The organic layer was separated, washed with water and brine, dried over sodium sulfate, filtered and evaporated in vacuo. The crude product obtained was purified by silica gel column chromatography using a gradient mixture of EA: Hexane (1:2 to 1:0) to give the pure title compound.

Yield: 19.0 g, 73% $^1$HNMR (DMSO-$d_6$): δ 4.78(s, 2H), 6.24(s, 1H), 6.29(s, 1H), 6.46(s, 1H), 7.18–7.38(m, 20H), 7.62(s, 1H), 7.85(s, 4H).

Step 2: 2-(2-Tritylamino)-thiazol-4-yl)-(Z)-2-[1,5-dibenzhydryloxy-4-pyridon-2-yl methoxy]-imino acetic acid.

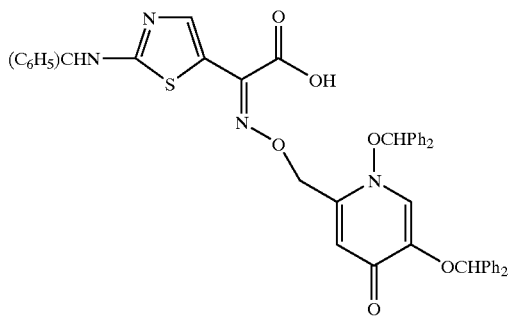

A solution of 1,5-dibenzhydryloxy-2-(N-phthalimido) oxymethyl-4-pyridone (10 g, 15.8 mmol) in ethanol (98%, 100 ml) was treated with hydrazine (0.76 ml). The mixture was heated to reflux for 1 h. and cooled to RT. The suspension thus obtained was filtered and the filtrate was evaporated to dryness and was treated with chloroform. The solid thus separated was filtered off, the mother liquors were concentrated and the residue obtained was dissolved in ethanol (98%) then treated with a solution of 2-oxo-2-[(N-tritylamino)thiazol-5-yl]acetic acid (6.38 g) in chloroform. The reaction mixture was stirred at room temperature for 18 h and evaporated in vacuo. The residue obtained was dissolved in ethyl acetate and diluted with hexanes. The solid separated was filtered and dried to give 2-(2-tritylamino) thiazol-4-yl)-(Z)-2-[1,5-dibenzhydryloxy-4-pyridon-2-yl methoxy]imino acetic acid.

Yield: 11.2 g, 79% $^1$HNMR (DMSO-$d_6$): δ 4.62(s, 2H), 6.03(s, 1H), 6.28(s, 1H), 6.40(s, 1H), 6.66(s, 1H), 7.18–7.35 (m, 35H), 7.48(s, 1H), 8.64(s, 1H).

Step 3: (3S)-trans-3-[2-(2-Tritylamino)thiazol-4-yl)-(Z)-2-{(1,5-dibenzhydryloxy-4-pyridon-2-yl methoxy)imino}-acetamido]-4-methyl-2-oxoazetidine-1-sulfonic acid.

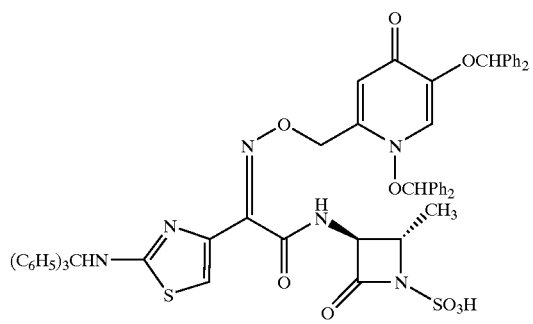

A mixture of (3S)-trans-3-amino-4-methyl-2-oxoazetidine-1-sulfonic acid [7.30 g, 40.52 mmol, J. Org. Chem., 47, 5160, (1982)], 2-(2-tritylamino)thiazol-4-yl)-(Z)-2-[1,5-dibenzhydryloxy-4-pyridon-2-yl methoxy]imino acetic acid (from step 36.50 g, 40.51 mmol), DCC (9.15 g, 44.34 mmol) and 1-hydroxybenzotriazole (5.47 g, 40.5 mmol) in dry DMF (400 ml) was stirred at room temperature for 30 min. and to this mixture NaHCO3 (3.40 g, 40.52 mmol) was added. The mixture was stirred under nitrogen at room temperature over night and filtered. The mother liquor was evaporated in vacuo to remove DMF and the residue obtained was dissolved in ethyl acetate and distilled water and adjusted to pH ~3. The organic layer was dried over anhydrous sodium sulfate, filtered and evaporated in vacuo.

The product thus obtained was purified over HP-20 column chromatography using a gradient mixture of water:acetonitrile (1:0 to 1:9) to give the title compound.

Silica gel column chromatography using a gradient mixture of ethyl acetate: methanol (1:0 to 9:1) gave the title compound Yield: 37.00 g, 85.9% $^1$HNMR (DMSO-$d_6$): δ 1.29(d, 3H, J=6.0 Hz), 3.54–3.61(m, 1H), 4.30–4.35(m, 1H), 4.70(s, 2H), 5.98(s, 1H), 6.29(s, 2H), 6.71(s, 1H), 7.25–7.35(m, 35H), 7.51(s, 1H), 8.83(s, 1H), 9.39(d, 1H, J=7.7 Hz).

Step 4: (3S)-trans-3-[(2-Amino)thiazol-4-yl)-(Z)-2-{(1,5-dihydroxy-4-pyridon-2-yl methoxy)imino}acetamido]-4-methyl-2-oxoazetidine-1-sulfonic acid.

A suspension of (3S)-trans-3-[-2-(2-tritylamino)thiazol-4-yl)-(Z)2-{(1,5-dibenzhydryloxy-4-pyridon-2-yl

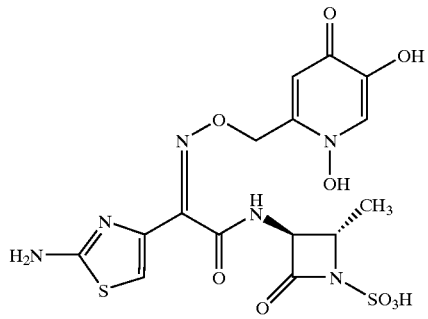

methoxy)imino}acetamido]-4-methyl-2-oxoazetidine-1-sulfonic acid (5.00 g, 4.703 mmol) in dry anisole (14 ml) at −10° C., under nitrogen was treated with trifluoroacetic acid (25 ml) and stirred at 0° C. for 2 hrs. The solvents were evaporated under reduced pressure and the residue was triturated with a mixture of ether-hexane and ethyl acetate (1:1:1). The solid thus obtained was filtered, washed with a mixture of ether-hexane and ethyl acetate (1:1:1) to give a solid. The above solid was further purified by HP-20 column chromatography using a gradient mixture of distilled water and acetonitrile (1:0 to 9:1) and the appropriate fractions were lyophilized to give the title compound.

Yield: 2.7 g, 92%; mp: 200° C. decomp. $^1$HNMR (DMSO d$_6$): δ 1.41(d, 3H, J=6.2 Hz), 3.70–3.80(m, 1H), 4.46(dd, 1H, J=2.4 Hz and 5.2 Hz), 5.30(s, 2H), 6.85(s, 1H), 7.05(s, 1H), 7.35(br, s, 2H), 8.17(s, 1H), 9.50(d, 1H, J=7.7 Hz).

Step 5: (3S)-trans-3-[(2-Amino)thiazol-4-yl)-(Z)-2-{(1,5-dihydroxy-4-pyridon-2-yl methoxy)imino}acetamido]-4-methyl-2-oxoazetidine-1-sulfonic acid, sodium salt.

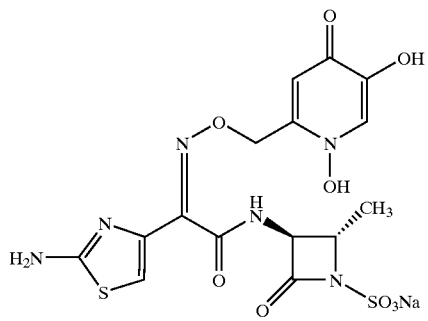

A suspension of (3S)-trans-3-[(Z)-(2-amino)thiazol-4-yl)-2-{(1,5-dihydroxy-4-pyridon-2-yl methoxy)imino}acetamido]-4-methyl-2-oxoazetidine-1-sulfonic acid (1.30 g, 2.66 mmol) in distilled water (15 ml) was cooled to ~5–6° C. and NaHCO3 (s, 0.223 g, 2.654 mmol) was added in portions with stirring. The clear solution thus obtained within 10 min. was filtered and lyophilized to give (3S)-trans-3-[{(2-amino)thiazol-4-yl)-(Z)-2-{(1,5-dihydroxy-4-pyridon-2-yl methoxy)imino}acetamido]-4-methyl-2-oxoazetidine-1-sulfonic acid, sodium salt.

Yield: 1.32 g, 97.13%. $^1$HNMR (DMSO-d$_6$): δ 1.42(d, 3H, J=6.1 Hz), 3.70–3.80(m, 1H), 4.48–4.53(m, 1H), 5.13(s, 2H), 6.64(s, 1H), 6.79(s, 1H), 7.24(br, s, 2H), 7.68(s, 1H), 9.52(d, 1H, J=7.0 Hz).

EXAMPLE 2

3-[2-(2-Aminothiazol-4-yl)-(Z)-2-{(1,5-dihydroxy-4-pyridon-2-yl methoxy)imino}-acetamido]-4-carbamoyloxymethyl-2-azetidinone-1-sulfonic acid, sodium salt Step 1: 3-[2-(2-Tritylamino)-thiazol-4-yl)-(Z)-2-{(1,5-dibenzhydryloxy-4-pyridon-2-yl methoxy)imino}acetamido]-4-carbamoyloxymethyl-2-azetidinone

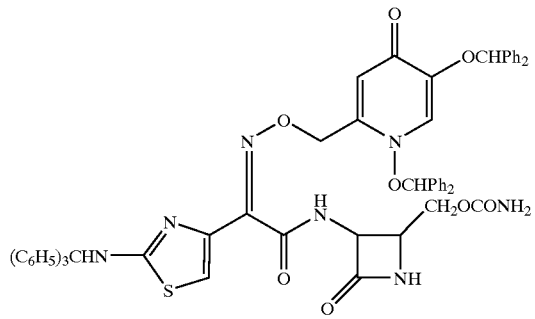

A solution of 2-(2-tritylamino)-thiazol-4-yl)-(Z)-2-[1,5-dibenzhydryloxy-4-pyridon-2-yl methoxy]imino acetic acid (0.34 g, 0.377 mmol) in dry DMF (20 ml) was treated with DCC (0.078 g, 0.377 mmol) and 1-hydroxybenzotriazole (0.050 g, 0.0377 mmol). The mixture was stirred under nitrogen at room temperature for 30 min. and to this mixture NaHCO₃ (0.032 g, 0.377 mmole) and 3-amino-4-carbamoyloxymethyl-2-azetidinone (0.06 g, 0.377 mmol) in DMF (5 ml) was added. The reaction mixture was stirred at room temperature for 18 hrs, and DMF was removed in vacuo. The product thus obtained was purified by silica gel column chromatography by a gradient mixture of ethyl acetate and methanol (10:1 to 9.5:0.5) to give the title compound.

Yield: 0.2 g, 97.13% $^1$HNMR (DMSO-d$_6$): δ 3.80–3.92 (m, 2H), 3.97–4.05(m, 1H), 4.70(s, 2H), 5.17–5.25(m, 1H), 6.00(s, 1H), 6.31(s, 1H), 6.53(br, s, 2H), 6.74(s, 1H), 7.24–7.38(m, 35H), 7.58(s, 1H), 8.50(s, 1H), 8.80(s, 1H), 9.29(d, 1H, J=9.0 Hz).

Step 2: 3-[{2-(2-Tritylamino)thiazol-4-yl)}-(Z)-2-{(1,5-dibenzhydryloxy-4-pyridon-2-yl methoxy)imino}acetamido]-4-carbamoyloxymethyl-2-azetidinone-1-sulfonic acid

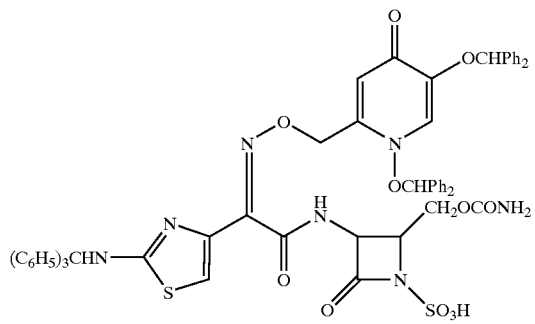

A solution of 3-[{2-(2-tritylamino)thiazol-4-yl)}-(Z)-2-{(1,5-dibenzhydryloxy-4-pyridon-2-yl methoxy)imino}acetamido]-4-carbamoyloxymethyl-2-azetidinone (0.25 g, 0.244 mmol) in pyridine (2 ml) was treated with sulfur trioxide-pyridine complex (0.153 g, 0.96 mmol) and the mixture was heated at 70° C. for 45 min. The reaction mixture was cooled to RT, treated with diethyl ether and the solid was filtered, washed with distilled water followed by ether and dried to give ciss-3-[{2-(2-tritylamino)thiazol-4-yl)}-(Z)-2-{(1,5-dibenzhydryloxy-4-pyridon-2-yl methoxy)imino}acetamido]-4-carbamoyloxy methyl-2-azetidinone-1-sulfonic acid.

Yield: 0.23 g, 85%

Step 3: 3-[2-(2-Tritylamino)-thiazol-4-yl)-(Z)-2-{(1,5-dibenzhydryloxy-4-pyridon-2-yl methoxy)imino}acetamido]-4-carbamoyloxymethyl-2-azetidinone-1-sulfonic acid, sodium salt.

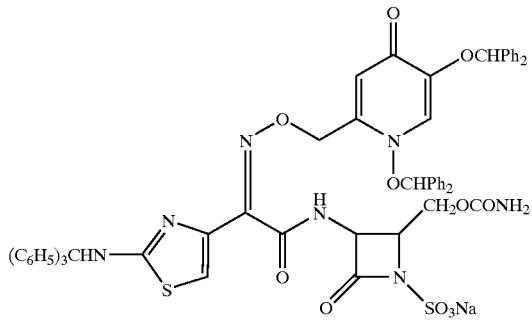

A suspension of 3-[2-(2-tritylamino)-thiazol-4-yl)-(Z)-2-{(1,5-dibenzhydryloxy-4-pyridon-2-yl methoxy)imino}acetamido]-4-carbamoyloxymethyl-2-azetidinone-1-sulfonic acid (0.390 g, 0.353 mmol) in distilled water (10 ml) was treated with $NaHCO_3$ (s, 0.050 g, 0.595 mmol) and stirred at RT for 30 min. and the clear solution was lyophilized. The solid obtained was purified by HP-20 column chromatography using a gradient mixture of dd. Water and acetonitrile (1:0 to 3:7), and the appropriate fractions were lyophilized to give the to give 3-[2-(2-tritylamino)-thiazol-4-yl)-(Z)-2-{(1,5-dibenzhydryloxy-4-pyridon-2-yl methoxy)imino}acetamido]-4-carbamoyloxymethyl-2-azetidinone-1-sulfonic acid, sodium salt.

Yield: 0.21 g, 52%

Step 4: 3-[2-(2-Aminothiazol-4-yl)-(Z)-2-{(1,5-dihydroxy-4-pyridon-2-yl methoxy)imino}acetamido]-4-carbamoyloxymethyl-2-azetidinone-1-sulfonic acid.

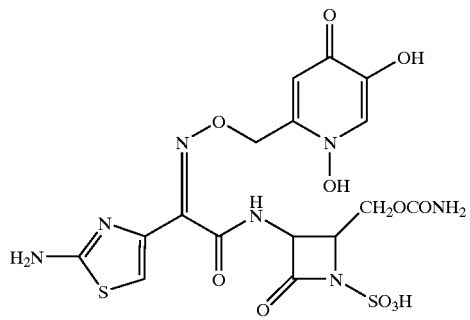

A suspension of 3-[2-(2-tritylamino)thiazol-4-yl)-(Z)-2-{(1,5-dibenzhydryloxy-4-pyridon-2-yl methoxy)imino}acetamido]-4-carbamoyloxymethyl-2-azetidinone-1-sulfonic acid, sodium salt (0.8 g, 0.874 mmol) in anisole (5 ml) under nitrogen atmosphere was cooled to ~0° C. and treated with trifluoroacetic acid (25 ml) and the mixture was stirred at less than 10° C. for 2 hrs and treated with ether. The solid separated was filtered, washed with acetone and dissolved in a mixture of acetonitrile/dd: $H_2O$ and freeze dried to give the title compound.

Yield: 0.34 g, 89%; mp: 190° decomp. $^1$HNMR (DMSO-$d_6$): δ 3.90–4.30(m, 3H), 5.22–5.40(m, 5H), 6.50(br, s, 2H), 6.82(s, 1H), 6.95(s, 1H), 7.33(br, s, 2H), 8.00(s, 1H), 9.45(d, 1H, J=7.5 Hz).

Step 5: 3-[2-(2-Aminothiazol-4-yl)-(Z)-2-{(1,5-dihydroxy-4-pyridon-2-yl methoxy)imino}acetamido]-4-carbamoyloxymethyl-2-azetidinone-1-sulfonic acid, sodium salt

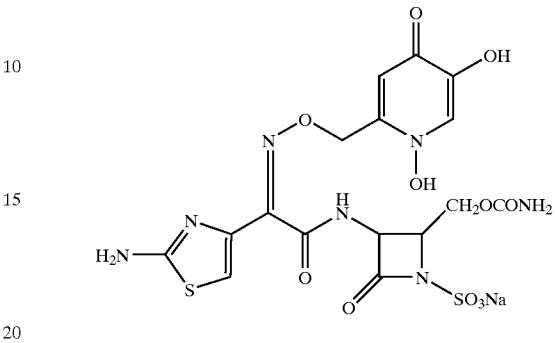

$NaHCO_3$ (s, 6 mg, 0.073 mmol) was added to a suspension of 3-[2-(2-Aminothiazol-4-yl)-(Z)-2-{(1,5-dihydroxy-4-pyridon-2-yl-methoxy)imino}-acetamido]-4-carbamoyloxymethyl-2-azetidinone-1-sulfonic acid (40 mg, 0.073 mmol) in distilled water. After stirring for 5 min. the mixture was freeze dried to give the title compound as a solid.

Yield: 30 mg, 71% $^1$HNMR (DMSO-$d_6$): δ 4.03–4.15(m, 2H), 4.20–4.33(m, 1H), 5.12(s, 2H), 5.26–5.37(m, 1H), 6.54(br, s, 2H), 6.70(s, 1H), 6.77(s, 1H), 7.24(br, s, 2H), 7.72(s, 1H), 9.38(d, 1H, J=7.5 Hz).

EXAMPLE 3

3-[2-(2-Aminothiazol-4-yl)-(Z)-2-{(1,5-dihydroxy-4-pyridon-2-yl-methoxy)imino}-acetamido]-4-fluoromethyl-2-azetidinone-1-sulfonic acid, sodium salt Step 1: 3-[2-(2-Tritylamino)-thiazol-4-yl)-(Z)-2-{(1,5-dibenzhydryloxy-4-pyridon-2-yl methoxy)imino}acetamido]-4-fluoromethyl-2-azetidinone-1-sulfonic acid.

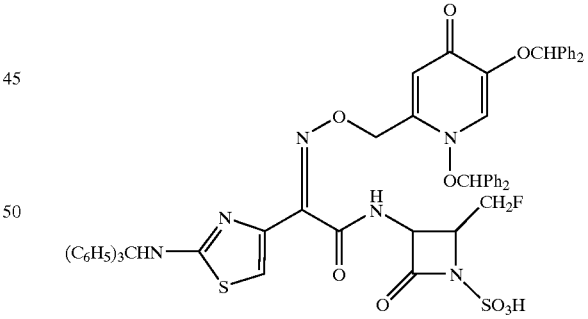

A solution of 3-(N-benzyloxycarbonyl)amino-4-fluoromethyl-2-azetidinone-1-sulfonic acid, tetrabutyl ammonium salt (0.5 g, 0.89 mmol) in DMF (20 ml) was treated with Pd—C (0.3 g) and the suspension was hydrogenated at 50 psi over 5 hrs. The suspension was filtered through celite and to the filtrate was added DCC (0.18 g, 0.89 mmol), 1-HBT (0.12 g, 0.89 mmol) followed by 2-{(2-tritylamino)-thiazol-4-yl}-(Z)-2-[1,5-dibenzhydryloxy-4-pyridon-2-yl methoxy]imino acetic acid (0.4 g, 0.89 mmol). The reaction mixture was stirred at RT for 18 hrs and evaporated in vacuo. The residue was dissolved in acetone treated with potassium nonafluoroborate (0.6 g) in acetone and stirred for a further 18 hrs. The solvents were evaporated and the residue was treated with a mixture of Ethyl acetate-Ether-Hexane (1:1:1). The solid separated was filtered and purified by silica gel column chromatography using a gradient mixture of Ethyl acetate and methanol (10:1 to 9:1) to give the title compound.

Yield: 0.22 g, 42.8% $^1$HNMR DMSO-d$_6$): δ 4.00–4.20(m, 2H), 4.40–4.50(m, 1H), 4.67(s, 2H), 5.16–5.24(m, 1H), 6.00(s, 1H), 6.32(s, 1H), 6.37(s, 1H), 6.67(s, 1H), 7.27–7.43 (m, 35H), 7.63(s, 1H), 8.85(s, 1H), 9.46(d, 1H, J=9.0 Hz).

Step 2: 3-[2-(2-Aminothiazol-4-yl)-(Z)-2-{(1,5-dihydroxy-4-pyridon-2-yl methoxy) imino}-acetamido]-4-fluoromethyl-2-azetidinone-1-sulfonic acid, sodium salt

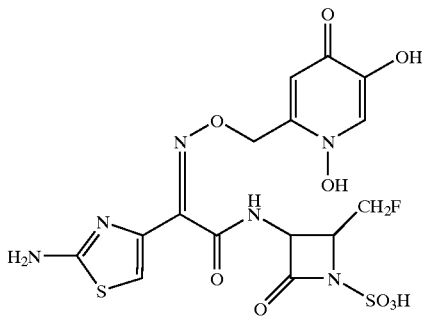

A suspension of 3-[2-(2-tritylamino)thiazol-4-yl)-(Z)-2-{(1,5-dibenzhydryloxy-4-pyridon-2-yl methoxy)imino}acetamido]-4-fluoromethyl-2-azetidinone-1-sulfonic acid (0.5 g, 0.46 mmol) in anisole (2 ml), under nitrogen at −10° C. was treated with trifluoroacetic acid (20 ml) and stirred at 5–10° C. for 2 hrs. The reaction mixture was evaporated in vacuo and the residue was triturated with a mixture of ether:ethyl acetate and hexanes (1:1:1). The solid separated was filtered, dissolved in acetonitrile, water mixture and freeze dried. The crude product obtained was further purified by HP-20 column chromatography using a gradient mixture of dd.H$_2$O and acetonitrile (1:0 to 9.4:0.6) to give 3-[2-(2-aminothiazol-4-yl)-(Z)-2-{(1,5-dihydroxy-4-pyridon-2-yl methoxy)imino}-acetamido]-4-fluoromethyl-2-azetidinone-1-sulfonic acid.

Yield: 80 mg, 34%; M.pt.: 200° C. decomp. $^1$HNMR (DMSO-d$_6$): δ 3.83–4.35(m, 2H), 4.47–4.63(m, 1H), 4.68–4.85(m, 1H), 5.28(s, 2H), 6.29(s, 1H), 7.03(s, 1H), 7.30(br, s, 3H), 8.12(s, 1H), 9.45(d, 1H, J=8.1 Hz).

Step 3: 3-[2-(2-Aminothiazol-4-yl)-(Z)-2-{(1,5-dihydroxy-4-pyridon-2-yl methoxy) imino}-acetamido]-4-fluoromethyl-2-azetidinone-1-sulfonic acid, sodium salt

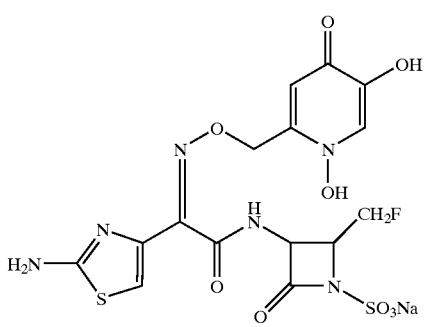

NaHCO$_3$ (s, 13 mg, 0.155 mmol) was added to a suspension of 3-[2-(2-Aminothiazol-4yl)-(Z)-2-{(1,5-dihydroxy-4-pyridon-2-yl-methoxy)imino}-acetamido]-4-fluoromethyl-2-azetidinone-1-sulfonic acid (80 mg, 0.158 mmol) in distilled water. The mixture was stirred for 5 min. and freeze dried to give 3-[2-(2-aminothiazol-4-yl)-(Z)-2-{(1,5-dihydroxy-4-pyridon-2-yl methoxy)imino}-3-acetamido]-4-fluoromethyl-2-azetidinone-1-sulfonic acid, sodium salt Yield: 75 mg, 89% $^1$HNMR (DMSO-d$_6$): δ 3.83–4.30(m, 2H), 4.47–4.64(m, 1H), 4.73–4.84(m, 1H), 5.13(s, 2H), 5.30(s, 1H), 6.55(s, 1H), 6.74(s, 1H), 7.27(br, s, 2H), 7.57(s, 1H), 9.57(br, s, 1H).

Test for Antibacterial Activity

The compounds of the present invention were tested for minimum inhibitory concentration (MIC) against the bacteria listed in Table-1 according to the standard microbroth dilution method as described in NCCLS document. The minimum inhibitory concentration is expressed in μg/ml.

TABLE 1

Antibacterial activity of the compounds of formula I

| Organisms | Tested compounds (MIC in μg/ml) | | | | |
|---|---|---|---|---|---|
| | 1 | 2 | 3 | Aztreonam | Carumonam |
| E. coli TEM-2 | 0.06 | 0.06 | 0.06 | 0.06 | 0.06 |
| K pneumoniae K-1150 | 0.13 | 0.06 | 0.06 | 0.06 | 0.06 |
| M Morganii K 1250 | 0.06 | 0.13 | 0.06 | 0.06 | 0.06 |
| C. freundii K 500 | 0.13 | 0.50 | 0.50 | 0.13 | 0.06 |
| E. cloaacae S 480-2 | 0.06 | 0.25 | 2.0 | 0.13 | 0.06 |
| P. aeruginosa CL 1267 | 0.06 | 0.06 | 0.06 | 32 | 8.0 |
| P. aeruginosa S 1598 | 0.13 | 0.13 | 0.13 | 32 | 8 |
| P. aeruginosa PD 2721 | 4.0 | 128 | 32 | 64 | 32 |

What we claim is:

1. A compound selected from the group consisting of a Syn isomer of a racemate and an optical isomer of 3-(heteroaryl acetamido)-2-oxo-axetidine-1-sulfonic acid and of formula I

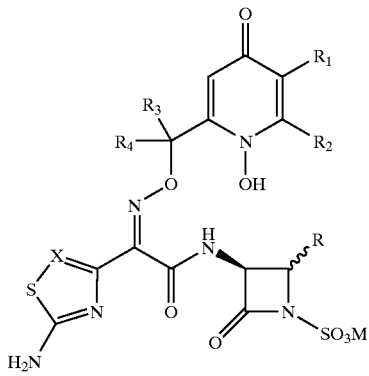

Wherein

M is a hydrogen or pharmaceutically acceptable salt forming cation;

X is CH, N or C-halogen;

R is C$_1$–C$_3$ alkyl which is unsubstituted or substituted with at least one of (a) a halogen atom (b) OR$_5$ wherein $R_5$ is hydrogen, $CONH_2$ provided that, when R is methyl, it cannot be substituted with both a halogen atom and $OR_5$;

$R_1$ and $R_2$ independently are OH, COOH, $CONH_2$, $NH_2$, dimethylamino, $OCH_3$, $NO_2$, CN, optionally substituted phenyl or $C_1$–$C_3$ alkyl; or $R_1$ and $R_2$ together are —O—CH=CH—$CH_2$—, —O—$CH_2$—$CH_2$—O—, —$CH_2$—$CH_2$—$CH_2$—, —$CH_2$—$CH_2$—$CH_2$—$CH_2$—, —CH=CH—CH=CH— or —CH=C(OH)—C(OH)=CH— which together with the carbon atoms to which they are bound form a 5 membered or six membered cyclic ring; and $R_3$ and $R_4$ independently are hydrogen, optionally substituted $C_1$–$C_3$ alkyl, optionally substituted phenyl or $C_3$–$C_6$ cycloalkyl; or $R_3$ and $R_4$ together with the C to which they are attached are $C_3$–$C_6$ cycloalkyl.

2. The compound of formula I as set forth in claim 1, wherein at least one of R, $R_1$, $R_2$, $R_3$, and $R_4$ are selected from the group consisting of methyl, ethyl, propyl and isopropyl.

3. The compound of formula I as set forth in claim 1, wherein R3 and R4 are independently a saturated alicyclic moiety having 3–6 carbon atoms selected from the group consisting of cyclopropyl, cyclobutyl, cyclopentyl and cyclohexyl.

4. The compound of formula I as set forth in claim 1, wherein the halogen atom is selected from the group consisting of fluorine, chlorine, and bromine.

5. The compound of formula I as set forth in claim 1, wherein the substitutents are 1, 2 or 3 substituents selected from OH, NH2, dimethylamino, halogen atom, $OCH_3$, COOH, $CONH_2$, $NO_2$ or CN.

6. A compound of formula I as set forth in claim 1, wherein the pharmaceutically acceptable salt forming cation is selected from the group consisting of alkali metals, alkaline earth metals, organic bases or basic amino acids.

7. A compound of formula I (I)

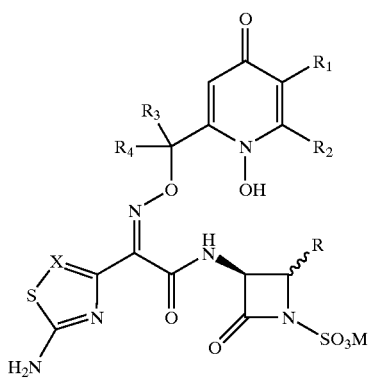

Wherein

M is a hydrogen or pharmaceutically acceptable salt forming cation;

X is CH;

R is $CH_3$, $CH_2F$ or $CH_2OCONH_2$;

$R_1$ is OH;

$R_2$ is Hydrogen; or $R_1$ and $R_2$ together are —CH=C(OH)—C(OH)=CH— which, together with the catons to which $R_1$ and $R_2$ are bound, forms a six member cyclic ring; and $R_3$ and $R_4$ independently are hydrogen; or $R_3$ and $R_4$ together with the C to which they are attached are cyclopropyl.

8. A pharmaceutical composition suitable for the treatment of bacterial infections in mammals comprising a compound selected from the group consisting of a Syn isomer of a racemate and an optical isomer of 3-(heteroaryl acetamido)-2-oxo-axetidine-1-sulfonic acid and of formula I (I)

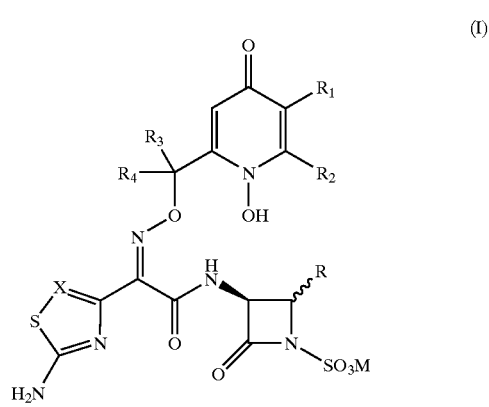

Wherein

M is a hydrogen or pharmaceutically acceptable salt forming cation;

X is CH, N or C-halogen;

R is $C_1$–$C_3$ alkyl which is unsubstituted or substituted with at least one of (a) a halogen atom (b) $OR_5$ wherein $R_5$ is hydrogen, $CONH_2$ or 2,5-dihydroxy-4-oxo-1,4-dihydro-pyridin-2-yl-carbonyl, wherein $C_1$ cannot be substituted with both a halogen atom and $OR_5$;

$R_1$ and $R_2$ independently are OH, COOH, $CONH_2$, $NH_2$, dimethylamino, $OCH_3$, $NO_2$, CN, optionally substituted phenyl or $C_1$–$C_3$ alkyl; or $R_1$ and $R_2$ together are —O—CH=CH—$CH_2$—, —O—$CH_2$—$CH_2$—O—, —$CH_2$—$CH_2$—$CH_2$—, —$CH_2$—$CH_2$—$CH_2$—$CH_2$—, —CH=CH—CH=CH— or —CH=C(OH)—C(OH)=CH— which together with the carbon atoms to which they are bound form a 5 membered or six membered cyclic ring; and $R_3$ and $R_4$ independently are hydrogen, optionally substituted $C_1$–$C_3$ alkyl, optionally substituted phenyl or $C_3$–$C_6$ cycloalkyl; or $R_3$ and $R_4$ together are $C_3$–$C_6$ cycloalkyl;

or a pharmaceutically acceptable salt of said compound; and wherein said composition further comprises a pharmaceutically acceptable carrier.

9. A method of treating a bacterial infection in a subject in need of such treatment comprising administering to said subject in need of such treatment a therapeutically effective amount of a compound selected from the group consisting of a Syn isomer of a racemate and an optical isomer of 3-(heteroaryl acetamido)-2-oxo-axetidine-1-sulfonic acid and of formula I

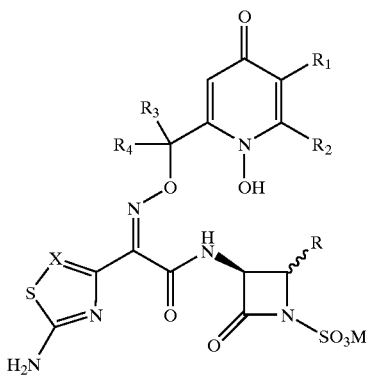

(I)

Wherein
- M is a hydrogen or pharmaceutically acceptable salt forming cation;
- X is CH, N or C-halogen;
- R is $C_1$–$C_3$ alkyl which is unsubstituted or substituted with at least one of (a) a halogen atom (b) $OR_5$ wherein $R_5$ is hydrogen, or, $CONH_2$, provided that, when R is methyl, it cannot be substituted with both a halogen atom and $OR_5$;
- $R_1$ and $R_2$ independently are OH, COOH, $CONH_2$, $NH_2$, dimethylamino, $OCH_3$, $NO_2$, CN, optionally substituted phenyl or $C_1$–$C_3$ alkyl; or
- $R_1$ and $R_2$ together are —O—CH=CH—$CH_2$—, —O—$CH_2$—$CH_2$O—, —$CH_2$—$CH_2$—$CH_2$—, —$CH_2CH_2$—$CH_2CH_2$—, —CH=CH—CH=CH— or —CH=C(OH)—C(OH)=CH— which together with the carbon atoms to which they are bound form a 5 membered or six membered cyclic ring; and
- $R_3$ and $R_4$ independently are hydrogen, optionally substituted $C_1$–$C_3$ alkyl, optionally substituted phenyl or $C_3$–$C_6$ cycloalkyl; or
- $R_3$ and $R_4$ together with the C to which they are attached are $C_3$–$C_6$ cycloalkyl.

10. The composition, according to claim 8, wherein said composition is formulated for oral use and comprises about 1 to 25 w/w % of a compound selected from the group consisting of a Syn isomer of a racemate and an optical isomer of 3-(heteroaryl acetamido)-2-oxo-axetidine-1-sulfonic acid and of formula I

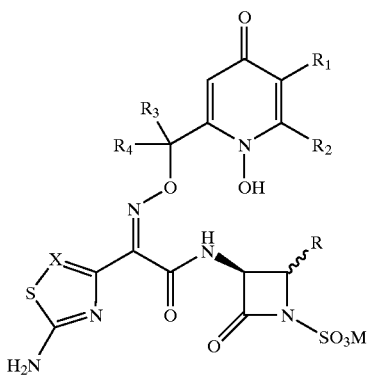

(I)

Wherein
- M is a hydrogen or pharmaceutically acceptable salt forming cation;
- X is CH, N or C-halogen;
- R is $C_1$–$C_3$ alkyl which is unsubstituted or substituted with at least one of (a) a halogen atom (b) $OR_5$ wherein $R_5$ is hydrogen, or, $CONH_2$, provided that, when R is methyl, it cannot be substituted with both a halogen atom and $OR_5$;
- $R_1$ and $R_2$ independently are OH, COOH, $CONH_2$, $NH_2$, dimethylamino, $OCH_3$, $NO_2$, CN, optionally substituted phenyl or $C_1$–$C_3$ alkyl; or
- $R_1$ and $R_2$ together are —O—CH=CH—$CH_2$—, —O—$CH_2$—$CH_2$—O—, —$CH_2$—$CH_2$—$CH_2$—, —$CH_2$—$CH_2$—$CH_2$—$CH_2$—, —CH=CH—CH=CH— or —CH=C(OH)—C(OH)=CH— which together with the carbon atoms to which they are bound form a 5 membered or six membered cyclic ring; and
- $R_3$ and $R_4$ independently are hydrogen, optionally substituted $C_1$–$C_3$ alkyl, optionally substituted phenyl or $C_3$–$C_6$ cycloalkyl; or
- $R_3$ and $R_4$ together with the C to which they are attached are $C_3$–$C_6$ cycloalkyl.

11. The composition, according to claim 8, wherein said composition is formulated for parental use and comprises about 0.1 to 5 w/w % of a compound selected from the group consisting of a Syn isomer of a racemate and an optical isomer of 3-(heteroaryl acetamido)-2-oxo-axetidine-1-sulfonic acid and of formula I

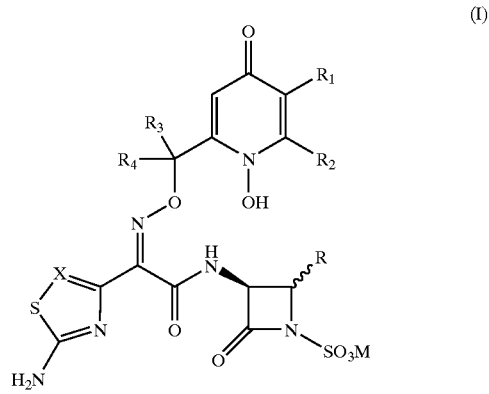

(I)

Wherein
- M is a hydrogen or pharmaceutically acceptable salt forming cation;
- X is CH, N or C-halogen;
- R is $C_1$–$C_3$ alkyl which is unsubstituted or substituted with at least one of (a) a halogen atom (b) $OR_5$ wherein $R_5$ is hydrogen, or, $CONH_2$, provided that, when R is methyl, it cannot be substituted with both a halogen atom and $OR_5$;
- $R_1$ and $R_2$ independently are OH, COOH, $CONH_2$, $NH_2$, dimethylamino, $OCH_3$, $NO_2$, CN, optionally substituted phenyl or $C_1$–$C_3$ alkyl; or
- $R_1$ and $R_2$ together are —O—CH=CH—$CH_2$—, —O—$CH_2$—$CH_2$—O—, —$CH_2CH_2$—$CH_2$—, —$CH_2$—$CH_2$—$CH_2$—$CH_2$—, —CH=CH—CH=CH— or —CH=C(OH)—C(OH)=CH— which together with the carbon atoms to which they are bound form a 5 membered or six membered cyclic ring; and
- $R_3$ and $R_4$ independently are hydrogen, optionally substituted $C_1$–$C_3$ alkyl, optionally substituted phenyl or $C_3$–$C_6$ cycloalkyl; or
- $R_3$ and $R_4$ together with the C to which they are attached are $C_3$–$C_6$ cycloalkyl.

12. The method of claim 9, wherein the therapeutically effective amount of the compound comprises an oral dosage of about 50 to 1500 mg/day of the compound for an adult in 2–4 divided doses.

13. The method of claim 9, wherein the therapeutically effective amount of the compound comprises an injection of about 100 mg of the compound.

14. The method of claim 9, wherein the therapeutically effective amount of the compound is diluted with physiological saline or glucose injection liquid.

15. The method of claim 9, wherein the therapeutically effective amount of the compound comprises a suppository containing about 1–1000 mg of the compound.

16. A method of producing a compound of formula I

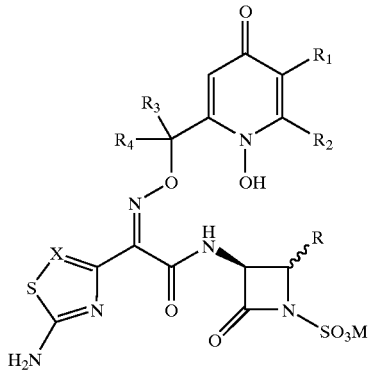

Wherein

M is a hydrogen or pharmaceutically acceptable salt forming cation;

X is CH;

R is $CH_3$, $CH_2F$ or $CH_2OCONH_2$;

$R_1$ is OH;

$R_2$ is Hydrogen; or $R_1$ and $R_2$ together are —CH=C(OH)—C(OH)=CH— which, together with the catons to which $R_1$ and $R_2$ are bound, forms a six member cyclic ring; and $R_3$ and $R_4$ independently are hydrogen; or $R_3$ and $R_4$ together with the C to which they are attached are cyclopropyl;

Wherein said method comprises:

(a) reacting a 3-amino-azetidine-2-one sulfonic acid of formula (II)

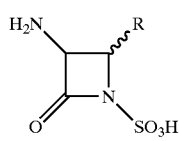

with a heteroaryl carboxylic acid of formula (III)

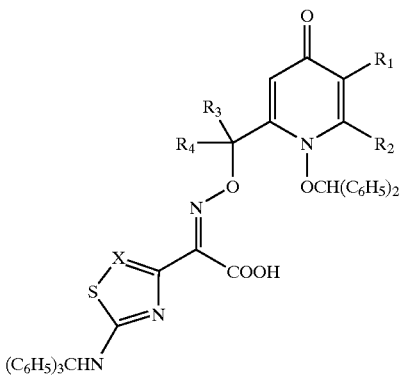

and (b) deprotecting the protecting group.

17. The compound of formula I as set forth in claim 1, wherein the optical isomer is a pure single R or S diasteroisomer at an asymmetric carbon atom present in the molecule.

18. A pharmaceutical composition comprising a compound of formula I

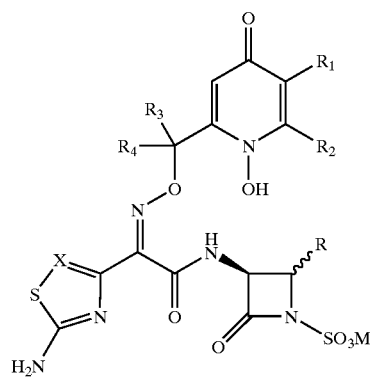

Wherein

M is a hydrogen or pharmaceutically acceptable salt forming cation;

X is CH;

R is $CH_3$, $CH_2F$ or $CH_2OCONH_2$;

$R_1$ is OH;

$R_2$ is Hydrogen; or $R_1$ and $R_2$ together are —CH=C(OH)—C(OH)=CH— which, together with the catons to which $R_1$ and $R_2$ are bound, forms a six member cyclic ring; and $R_3$ and $R_4$ independently are hydrogen; or $R_3$ and $R_4$ together with the C to which they are attached are cyclopropyl.

19. A method of treating a bacterial infection in a subject in need of such treatment comprising administering to said subject in need of such treatment a therapeutically effective amount of a compound selected from the group consisting of a Syn isomer of a racemate and an optical isomer of 3-(heteroaryl acetamido)-2-oxo-axetidine-1-sulfonic acid and of formula I

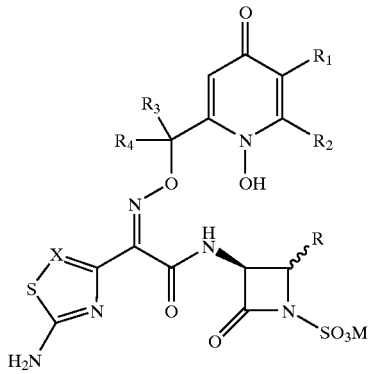

Wherein

M is a hydrogen or pharmaceutically acceptable salt forming cation;

X is CH;

R is $CH_3$, $CH_2F$ or $CH_2OCONH_2$;

$R_1$ is OH;

$R_2$ is Hydrogen; or $R_1$ and $R_2$ together are —CH=C(OH)—C(OH)=CH— which, together with the catons to which $R_1$ and $R_2$ are bound, forms a six member cyclic ring; and $R_3$ and $R_4$ independently are hydrogen; or $R_3$ and $R_4$ together with the C to which they are attached are cyclopropyl.

* * * * *

UNITED STATES PATENT AND TRADEMARK OFFICE
CERTIFICATE OF CORRECTION

PATENT NO. : 6,916,803 B2
DATED : July 12, 2005
INVENTOR(S) : Micetich et al.

It is certified that error appears in the above-identified patent and that said Letters Patent is hereby corrected as shown below:

Column 21,
Line 1, "hydrogen," should read -- hydrogen or, --.
Line 20, "are selected" should read -- is selected --.
Line 33, "from OH," should read -- from the group consisting of OH, --.
Line 34, "$NO_2$ or CN." should read -- $NO_2$ and CN. --.

Column 23,
Line 31, "—O—$CH_2$—$CH_2O$—," should read -- —O-$CH_2$-$CH_2$-O-, --.
Line 32, "—$CH_2CH_2$—$CH_2CH_2$—," should read -- -$CH_2$-$CH_2$-$CH_2$-$CH_2$-, --.

Column 24,
Line 58, "—$CH_2CH_2$—$CH_2$—," should read -- -$CH_2$-$CH_2$-$CH_2$-, --.

Signed and Sealed this

Thirtieth Day of August, 2005

JON W. DUDAS
*Director of the United States Patent and Trademark Office*